United States Patent
Stradella

(10) Patent No.: US 7,363,924 B2
(45) Date of Patent: Apr. 29, 2008

(54) FLUID PRODUCT DISPENSING DEVICE

(75) Inventor: Giuseppe Stradella, Camogli (IT)

(73) Assignee: Valois S.A.S., Le Neubourg (FR)

( * ) Notice: Subject to any disclaimer, the term of this patent is extended or adjusted under 35 U.S.C. 154(b) by 435 days.

(21) Appl. No.: 10/416,794

(22) PCT Filed: Nov. 23, 2001

(86) PCT No.: PCT/FR01/03706

§ 371 (c)(1),
(2), (4) Date: May 15, 2003

(87) PCT Pub. No.: WO02/41939

PCT Pub. Date: May 30, 2002

(65) Prior Publication Data

US 2004/0025869 A1 Feb. 12, 2004

(30) Foreign Application Priority Data

Nov. 24, 2000 (FR) .................................. 00 15337

(51) Int. Cl.
*A61M 11/00* (2006.01)
(52) U.S. Cl. .............................. 128/200.23; 128/200.14
(58) Field of Classification Search ........... 128/200.18, 128/200.23, 203.12, 203.15, 203.23, 200.21, 128/200.14, 200.22; 222/402.24, 402.2; 239/350

See application file for complete search history.

(56) References Cited

U.S. PATENT DOCUMENTS 3,356,088 A * 12/1967 Nelson .................. 128/200.23
4,414,972 A   11/1983 Young et al.
4,819,834 A *  4/1989 Thiel .......................... 222/355
5,027,808 A    7/1991 Rich et al.
5,215,079 A *  6/1993 Fine et al. ............. 128/200.14

(Continued)

FOREIGN PATENT DOCUMENTS

EP     0 490 797 A    6/1992

(Continued)

OTHER PUBLICATIONS

"L' Aerosol-Doseur Prolair Authohaler" Annales Francaises de Chronometrie et de Microtechnique, FR, Obstervato Ire de Besancon. Besancon, vol. 47, 1998, pp. 115-121, XP000830922 ISSN:0294-1228.

*Primary Examiner*—Justine R. Yu
*Assistant Examiner*—Annette Dixon
(74) *Attorney, Agent, or Firm*—Sughrue Mion, PLLC

(57) ABSTRACT

A fluid dispenser device having a reservoir (1), a metering valve (2) having a valve member (3), and an automatic trigger system for actuating the valve. The trigger system has a resilient element (10) moved manually into a cocked position. The trigger system releases the resilient element (10) and moves to an actuating position by moving the valve member (3) towards its dispensing position. The resilient element (10) is returned manually to its rest position. The fluid dispenser device includes a valve member release system co-operating with the reservoir (1) or with the valve member (3) so that, after dispensing the fluid, the valve member (3) is released from the force exerted by the resilient element (10), so that, after the device is actuated, the valve member (3) is returned to its rest position by the return spring of the valve, independently of the position of the resilient element.

17 Claims, 9 Drawing Sheets

U.S. PATENT DOCUMENTS

| | | | |
|---|---|---|---|
| 5,347,998 A * | 9/1994 | Hodson et al. | 128/200.23 |
| 5,608,647 A * | 3/1997 | Rubsamen et al. | 700/281 |
| 5,622,162 A * | 4/1997 | Johansson et al. | 128/200.14 |
| 5,694,919 A * | 12/1997 | Rubsamen et al. | 128/200.14 |
| 5,709,202 A * | 1/1998 | Lloyd et al. | 128/200.14 |
| 5,735,263 A * | 4/1998 | Rubsamen et al. | 128/200.14 |
| 6,223,744 B1 * | 5/2001 | Garon | 128/200.14 |
| 6,328,035 B1 * | 12/2001 | Wakefield et al. | 128/203.23 |
| 6,354,290 B1 * | 3/2002 | Howlett | 128/200.23 |
| 6,637,430 B1 * | 10/2003 | Voges et al. | 128/200.14 |
| 6,672,304 B1 * | 1/2004 | Casper et al. | 128/200.23 |

FOREIGN PATENT DOCUMENTS

| | | |
|---|---|---|
| FR | 2 701 399 A | 8/1994 |
| WO | 98 52634 A | 11/1998 |
| WO | 99 44662 A | 9/1999 |

\* cited by examiner

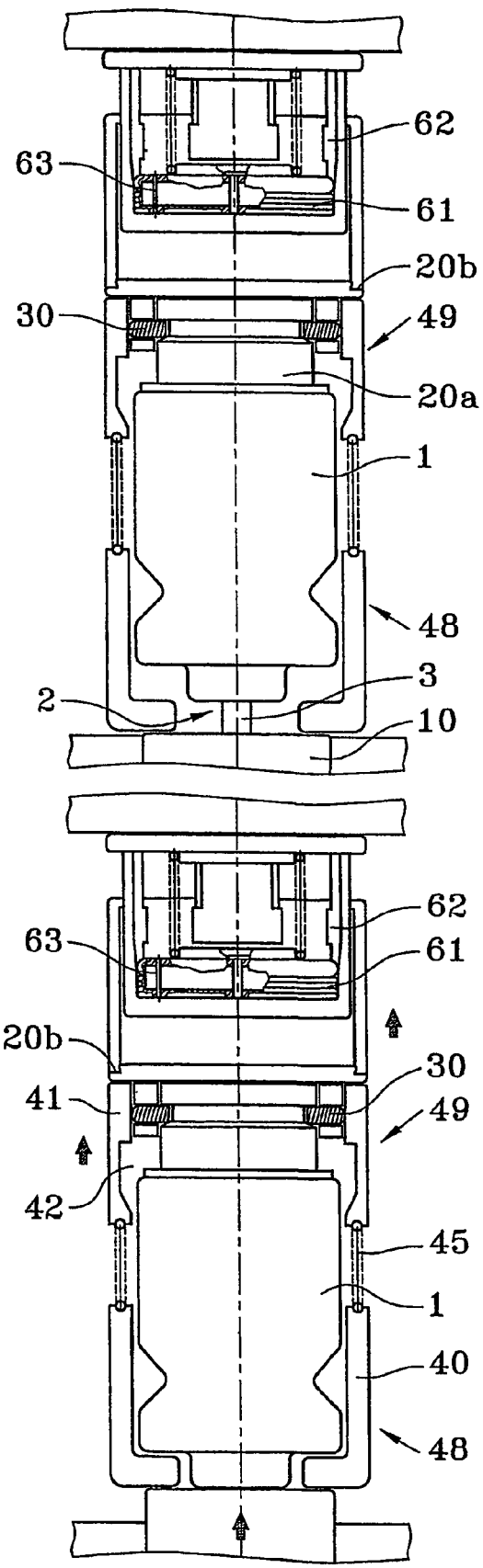
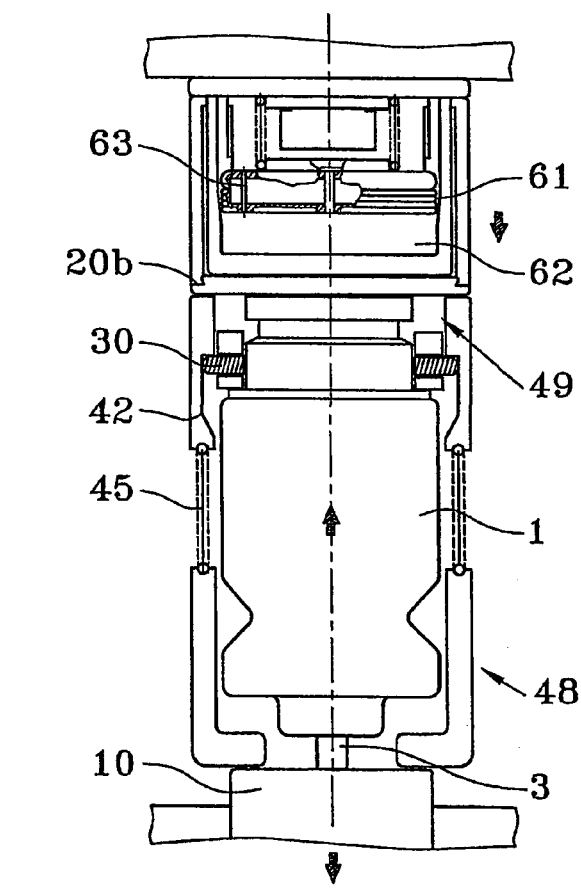
FIG.15
FIG.16
FIG.17

FLUID PRODUCT DISPENSING DEVICE

FIELD OF THE INVENTION

The present invention relates to a fluid dispenser device, and more particularly to an inhaler device having a metering valve, and of the Metered Dose Inhaler (MDI) type, in which the metering valve is actuated by the user inhaling.

BACKGROUND OF THE INVENTION

Such inhalers, generally referred to as Breath-Actuated Inhalers (BAIs) and using metering valve systems (MDI systems), are usually based on a trigger mechanism having a spring, said spring being released by a suitable device when the user inhales. Loading or compressing the spring is usually achieved by actuating a lever, e.g. when opening the lid on the mouthpiece of the inhaler, and, on inhaling, the force from the spring is directed against the reservoir or against the metering valve, enabling the valve to be actuated by moving the valve member relative to the reservoir. This is made possible by the fact that one of the elements comprising the valve member and the reservoir which is not subjected to the drive from the pre-cocked spring, is held stationary inside the device. As a result, after it has been actuated, and after the fluid contained in the reservoir has been dispensed, the metering valve remains compressed with the valve member in its actuating position until the load on the spring is released, which occurs only once the lid of the mouthpiece has been closed again.

The above-described structure is the source of a problem which is related to the manner in which most metering valves operate. Such a valve generally has a return spring and a metering chamber which is filled with a mixture made up of the fluid, in general medication, and of the liquefied propellant gas. The metering chamber is filled under gravity and only when the valve member moves from its dispensing position to its rest position, i.e. when the force applied on the valve by the spring of the trigger system is released. This therefore requires the tension of the spring to be released when the device is in a position suitable for enabling the metering chamber of the valve to be filled by gravity. The position required in order for the metering chamber to be filled effectively and fully is the in-use position of the inhaler, in which position the reservoir is generally disposed above the metering valve, the user having the mouthpiece in the mouth for the purpose of inhaling the metered quantity or "dose" of fluid dispensed.

As of the end of dispensing of the dose of fluid, when the user withdraws the device from the mouth, there is a high probability that the inhaler is no longer in the position required for effective filling, and there is a high risk that the user might close the lid of the mouthpiece while the inhaler device is in a position that is unsuitable for filling the metering chamber fully.

OBJECTS OF THE INVENTION

An object of the present invention is to provide a fluid dispenser device that does not reproduce the above-mentioned drawbacks.

An object of the present invention is thus to provide a fluid dispenser device that guarantees that the metering chamber of the valve is filled in a position suitable for ensuring that the metering chamber is filled fully and reliably.

Another object of the invention is to provide such a fluid dispenser device that enables the metering chamber of the metering valve to be filled after the dose of fluid has been dispensed, independently of the position of the spring of the trigger mechanism for triggering the device.

A further object of the invention is to provide such a fluid dispenser device that is simple and inexpensive to manufacture and assemble.

The present invention thus provides a fluid dispenser device comprising a reservoir containing fluid and a propellant gas, a metering valve mounted on said reservoir and comprising a metering chamber and a valve member mounted to move between a dispensing position and a rest position, and an automatic trigger system for actuating said valve and that is preferably actuated by the user inhaling, said trigger system comprising a resilient element formed by or secured to a spring, said resilient element being moved manually by the user into a cocked position in which it is held under tension, actuation of the trigger system releasing said resilient element which then moves to an actuating position while exerting a force adapted to moving the valve member of the valve towards its dispensing position, said resilient element then being returned manually by the user from its actuating position to its rest position in which it no longer urges said valve member towards its dispensing position, said fluid dispenser device being characterized in that it further comprises a valve member release system which co-operates with the reservoir or with the valve member of the valve so that, after dispensing the fluid contained in the metering chamber of the valve, said valve member is released from the force exerted by said resilient element of the trigger system, so that, after the device is actuated, said valve member is returned to its rest position by the return spring of the valve, independently of the position of said resilient element.

Preferably, said valve member release system comprises a locking element co-operating with one of the valve member and the fluid reservoir, said locking element being mounted to move between a locking position, in which the valve member can be brought into its dispensing position by said resilient element of the trigger system, and an unlocking position, in which the valve member is brought into its rest position independently of the position of said resilient element, said locking element being urged to its unlocking position after the trigger system has been actuated.

In a first embodiment of the present invention, the valve member release system includes a retaining member that can be moved from a retaining position in which it retains said locking element in its locking position, and a non-retaining position in which it does not retain said locking element in its locking position, said retaining member being moved towards its non-retaining position when the valve member reaches its dispensing position.

Advantageously, said valve member release system includes a control element co-operating firstly with the valve member and secondly with the retaining member so that when the valve member reaches its dispensing position, the control element makes it possible to move the retaining member to its non-retaining position so that the locking element is moved into its unlocking position, and the valve member is returned to its rest position by the return spring of the valve.

Advantageously, said retaining member is resiliently deformable and said control element includes a first inside diameter co-operating with the retaining member to prevent it from deforming and thus to hold it in its retaining position, and a second inside diameter greater than said first inside diameter, which co-operates with said retaining member when the valve member reaches its dispensing position, then making it possible to deform said retaining member towards its non-retaining position.

In a second embodiment of the present invention, said locking element includes a brake device adapted to slow down the movement of said locking element towards its unlocking position, after the trigger system has been actuated.

Advantageously, said brake device is mechanical and includes a moving element connected to said locking element, and that slides with friction against or between one or more brake members.

Advantageously, said moving element is a preferably serrated rod, and said brake comprises two preferably elastomer wheels, said rod sliding with friction between said wheels.

Advantageously, each wheel is secured to a respective deformable arm so that when the rod slides between said wheels, each arm deforms so that said wheels come towards each other, thereby increasing the friction exerted on said rod to perform the braking.

In a variant of said second embodiment of the invention, said brake device is pneumatic and/or hydraulic.

Advantageously, said brake device includes a piston connected to said locking element, said piston sliding in leaktight manner in a chamber, said chamber or said piston being provided with a small orifice so that gas or liquid can flow only slowly into or out from said chamber, thereby causing said piston to move slowly.

In a third embodiment of the present invention, the valve member release system comprises a first locking element moved to its unlocking position when the valve member reaches its dispensing position, and a second locking element provided with a brake system, and urged into its unlocking position by said first locking element when it is in the unlocking position, so that the brake system is actuated only once the valve member is in its dispensing position.

Advantageously, said first locking element cooperates firstly with the end-wall of the reservoir and secondly with said second locking element which is secured to said brake.

In a fourth embodiment of the present invention, said valve member release system includes a delay system adapted to release the valve member of the metering valve after a predetermined delay time after the valve member has reached its dispensing position.

Advantageously, the valve member release system comprises a first locking element retained by a retaining member itself co-operating with a control element, said control element having a first portion secured to the resilient element of the trigger system, and a second portion co-operating firstly with said retaining member, and secondly with a second locking element provided with a brake system, a resilient member of low stiffness, such as a spring, being interposed between said first and second portions of the control element, so that said first locking element can move towards its unlocking position only after a delay time predetermined to enable said valve member of the valve to return to its rest position, said delay time corresponding to the time necessary for the second locking element to move into its unlocking position, against said brake system under drive from said resilient member, thereby moving said second portion of the control element into the position in which the retaining member can deform into its non-retaining position, so as to enable the first locking element to move into its unlocking position.

In a variant, said delay system is electronic or electromechanical.

BRIEF DESCRIPTION OF THE DRAWINGS

Other characteristics and advantages of the present invention appear more clearly on reading the following detailed description of embodiments of it, described with reference to the accompanying drawings which are given by way of non-limiting example, and in which:

FIG. 15 is a diagrammatic section view of a fourth embodiment of the present invention, before the device is actuated;

FIG. 16 is a view similar to FIG. 15, while the device is being actuated; and FIG. 17 is a view similar to FIGS. 15 and 16, after the device is actuated.

DETAILED DESCRIPTION OF EXEMPLARY EMBODIMENTS

The present invention is applicable to all types of breath-actuated inhalers (BAIs), and even though several embodiments are described with reference to such an inhaler, in which the spring of the breath-actuated trigger system acts on the valve member, clearly it also applies to devices in which the spring acts on the end-wall of the reservoir. Whether the resilient force for actuating the valve is exerted on the valve member or on the reservoir has no direct influence on the present invention, which is applicable in both cases, the present invention serving to enable the valve member to return to its rest position independently of the position or the state of said spring of the breath-actuated trigger system.

The following description is given with reference to a device of the type disclosed in Document WO 99/44662, that document being incorporated by way of reference into the present invention as regards operation of the breath-actuated trigger system of the fluid dispenser device.

A first embodiment of the invention is described with reference to FIGS. 1 and 2. In this first embodiment, a system is provided for releasing the valve member that acts automatically when the valve member reaches its dispensing position, in which it delivers the dose of fluid contained in the metering chamber.

Figure 1:
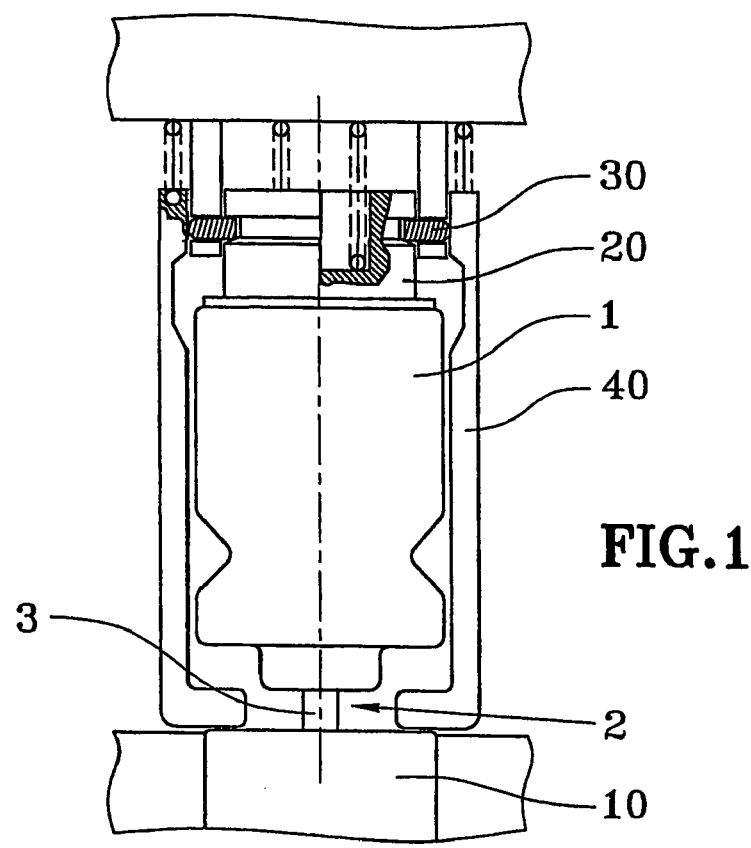
FIG. 1 is a partially-cutaway diagrammatic section view of first embodiment of a fluid dispenser device of the present invention, before the valve is actuated.

FIG. 1 very diagrammatically shows a fluid reservoir 1 to which a metering valve 2 is fitted in any desired manner, said metering valve 2 having a valve member 3 mounted to move between a rest position and a dispensing position. The metering valve 2 has a metering chamber (not shown) which empties when the valve member 3 is in its dispensing position, and which fills under gravity when the valve member 3 returns from its dispensing position to its rest position. Said valve 3 co-operates with a resilient element 10 which is part of a breath-actuated trigger system, and which is constituted by or secured to a spring (not shown in FIGS. 1 and 2), said spring being cocked by the user before the device is used, so that, when the user inhales, the resilient element 10 is released and can exert a force on the valve member 3 so as to actuate the metering valve. During this process in which the valve member 3 moves from its rest position to its actuating position, the reservoir 1 is held stationary in the body of the device.

Figure 2:
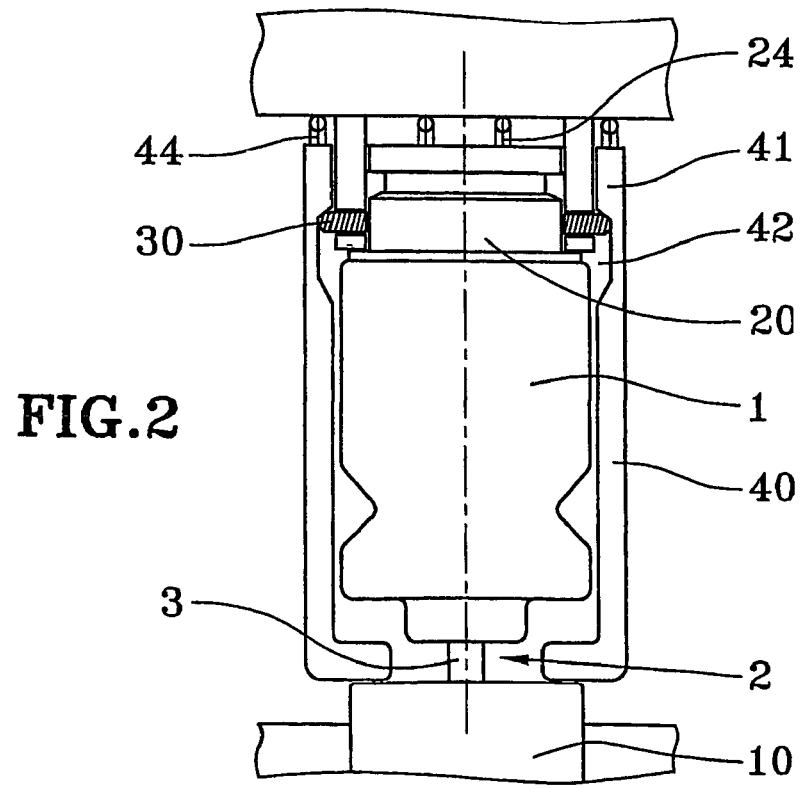
FIG. 2 is a view similar to the FIG. 1 view, after the valve is actuated.

The valve member release system has a locking element 20 which, in the example shown in FIGS. 1 and 2, co-operates with the end-wall of the reservoir 1. This locking element 20 is retained in its locking position by a retaining member 30, which, in the example shown in FIGS. 1 and 2, is implemented in the form of a split ring that can be deformed radially outwards. In a variant, the retaining member could be implemented in the form of one or more outwardly deformable resilient catches. The split ring 30 co-operates with said locking element 20 to hold it in its locking position, in which it holds the reservoir 1 stationary inside the device. A control element 40 is connected at one end to the resilient member 10 of the breath-actuated trigger system and co-operates at the other end with said retaining element 30. Thus, as shown in FIGS. 1 and 2, the control element 40 is moved at the same time as the resilient element 10, and thus at the same time as the valve member 3 when the metering valve is actuated. It is implemented in the form of a sleeve which surrounds said ring 30 externally, and which has a first diameter 41 and a second diameter 42 greater than said first diameter. The first diameter 41 of control element 40 co-operates with the retaining member 30 before the device is actuated, and the second diameter 42 cooperates with said retaining member 30 after the device is actuated, when the valve member 3 is in its dispensing position. Whereupon, the retaining member 30 can deform radially outwards inside the second diameter 42 of the control element 40 to release the locking element 20. In a variant, the second diameter portion of the control element may be implemented in the form of an opening, the essential requirement being for it to be possible for the retaining member to deform into its non-retaining position. The locking element 20 can then slide axially under the effect of the force exerted by the return spring (not shown) of the metering valve, so that the metering valve returns to its rest position as soon as the retaining member 30 is moved into its non-retaining position shown in FIG. 2. The valve member 3 is always locked by the resilient element 10 of the trigger system, so long as said resilient element is not returned manually by the user to its rest position, but it is the reservoir 1 that is then free to move so as to enable the valve member 3 to return to its rest position after fluid has been dispensed. It is thus the element that is stationary during actuation, i.e. the reservoir in this example, that moves to release the valve member.

Thus, in the embodiment shown in FIGS. 1 and 2, at the time when the valve member 3 reaches its dispensing position and delivers the fluid contained in the metering chamber of the metering valve 2, the reservoir 1 is released, it being possible for the locking element 20 to move to its unlocking position, the valve member 3 then returning to its rest position, thereby enabling the metering chamber to be filled while the device is still in the mouth of the user, and guaranteeing that such filling takes place in the required position, as shown in the drawings, with the metering valve 2 disposed below the reservoir 1, filling then taking place by gravity.

Advantageously, filling takes place as of the end of dispensing of the preceding dose, i.e. very rapidly. This makes it possible to avoid any problem of metering out a dose that is too large, which could occur if there is a waiting time with the device in the upside down position, in particular when metering out suspensions.

Advantageously, it is possible to provide a return spring 24 for the locking element 20, and a return spring 44 for the control element 40, so that, when the user returns the resilient element 10 manually to its rest position, the control element 40 is returned automatically to its initial position by said return spring 44, and similarly, the locking element 20 is returned to its locking position by the return spring 24, the retaining member 30 returning to its position inside the groove in said locking element 20 to lock said locking element in the locking position, and the first diameter 41 of the control member comes to lock the retaining member in the retaining position.

Figure 3:
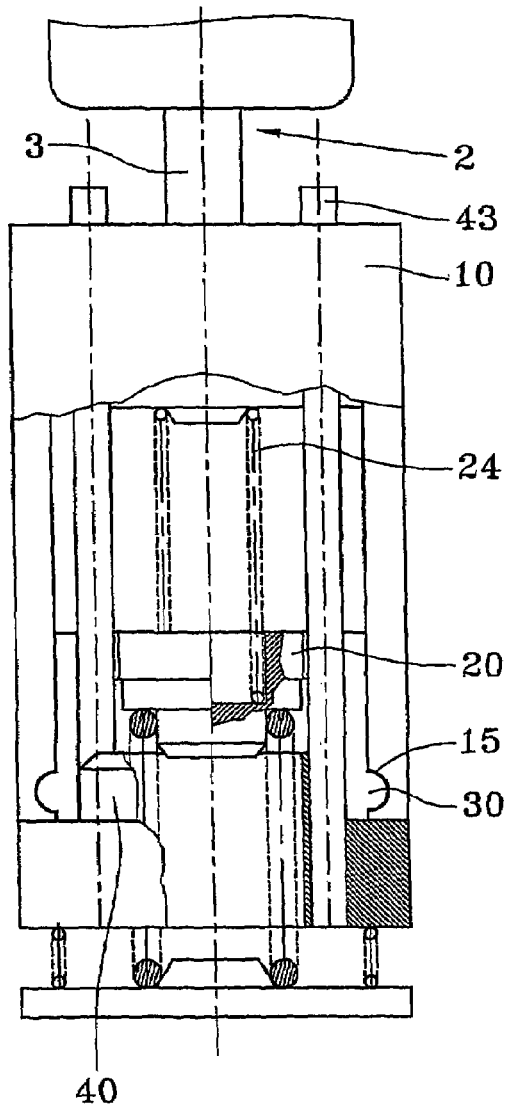
FIG. 3 is a partially-cutaway diagrammatic section view of a variant of the first embodiment of the invention, before the valve is actuated.
Figure 4:
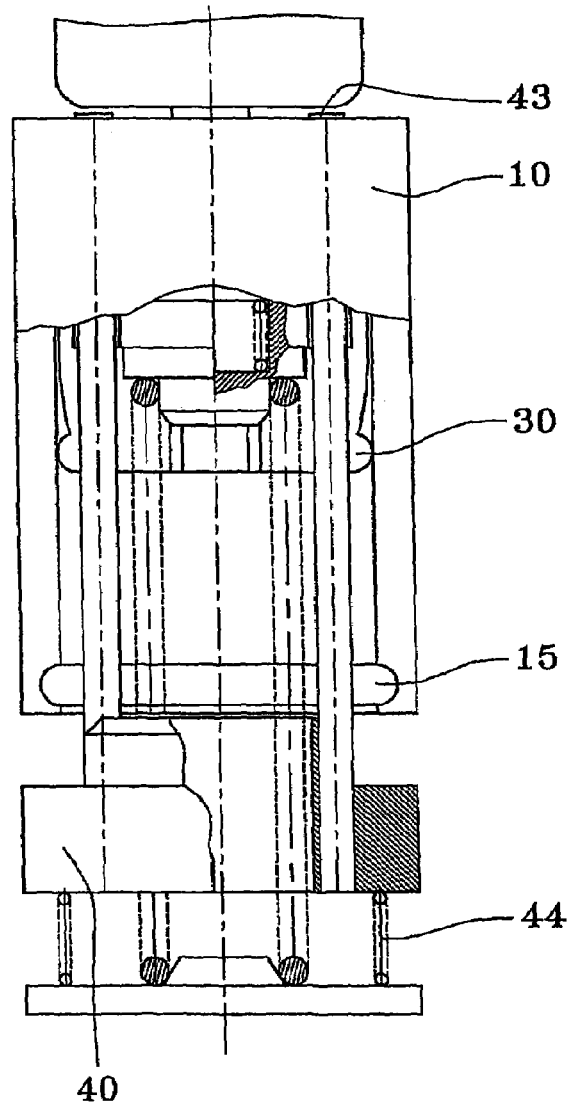
FIG. 4 is a view similar to the FIG. 3 view, after the valve is actuated.

FIGS. 3 and 4 show a variant of the embodiment shown in FIGS. 1 and 2. In this variant, the valve member release system does not act on the end-wall of the reservoir 1, but rather it co-operates directly firstly with the resilient element 10 of the breath-actuated trigger system, and secondly with the valve member 3. In this case, the resilient element 10 is hollow, at least in part, and it incorporates a locking element 20 which is provided with flexible arms which, at their ends, are provided with radial projections 30 that form the retaining member for the valve member release system. The projections 30, and thus the locking element 20 are held in the locking position by the control element 40 which locks the flexible arms in a straight position in which the projections 30 are forced into engagement with a groove 15 formed in the inside walls of the resilient element 10. The control element 40 is provided with one or more rods 43 which pass through suitable openings provided in the locking element 20 and through the resilient element 10 of the breath-actuated trigger system, and which project from said resilient element 10 towards the reservoir 1 of the metering valve 2.

Thus, in this variant, the valve member release system is implemented inside said resilient element 10 of the breath-actuated trigger system. At the end of the stroke of the valve member 3, when said valve member reaches the dispensing position and dispenses the dose of fluid contained in the metering chamber, the ends of the rods 43 reach the neck of the reservoir or the fixing ring for fixing the metering valve to said reservoir, and are moved thereby downwards (as shown in FIGS. 3 and 4). This causes the control element 40 to move from its position shown in FIG. 3 to its position shown in FIG. 4, in which it no longer co-operates with the resilient arms of the locking element 20, and thus with the projections 30 at the ends of said arms, so that said locking element 20 is released and can move to its unlocking position by said arms flexing to interrupt the interaction between the projections 30 and the corresponding groove 15 provided in the internal wall of the resilient element 10. The result is that the locking element 20 is propelled upwards (as shown in FIGS. 3 and 4), thereby releasing the tension applied to the spring of the resilient element 10. Thus, the valve member 3 of the metering valve can return to its rest position under drive from the return spring of the valve.

When the user then returns the resilient element 10 to its rest position, in particular by re-closing the lid on the mouthpiece (not shown), the locking element 20 takes up its original position again (shown in FIG. 3), by means of the return spring 24 provided for this purpose. While the locking element 20 is returning to its rest position, it pushes the control element 40 downwards (as shown in FIGS. 3 and 4), which control element then also reaches the rest position (shown in FIG. 3) again, in which the projections 30 co-operate again with the corresponding groove 15, by means of the return spring 44 provided for this purpose.

Figure 6:
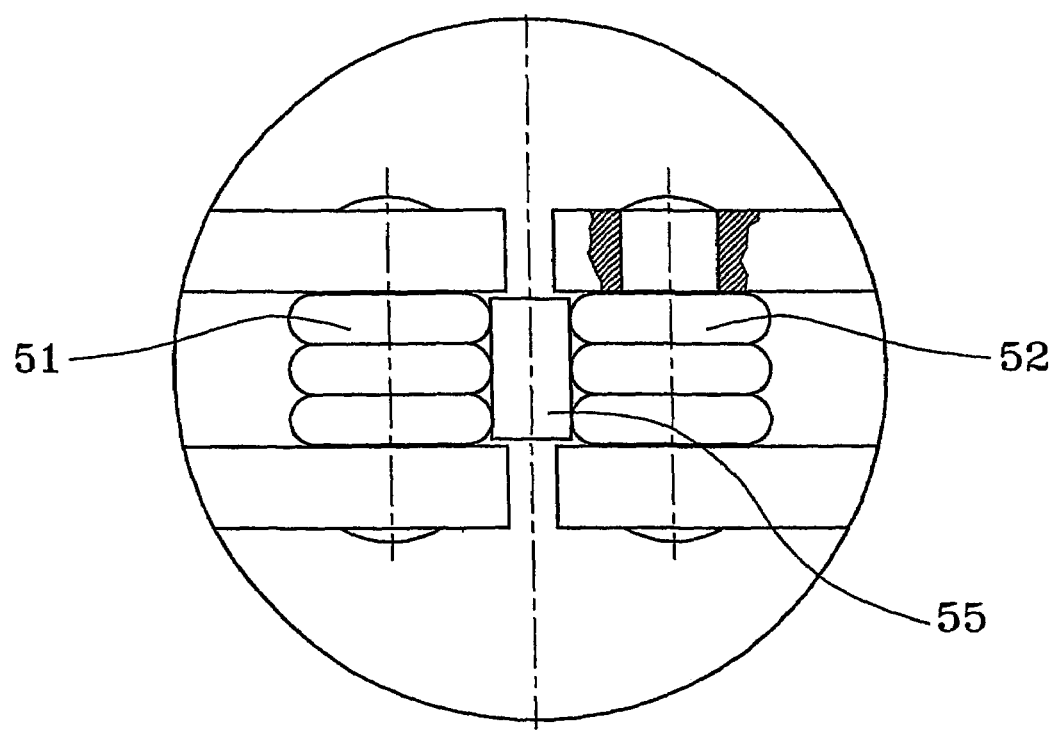
FIG. 6 is an enlarged detail view of the brake system shown in FIG. 5.
Figure 7:
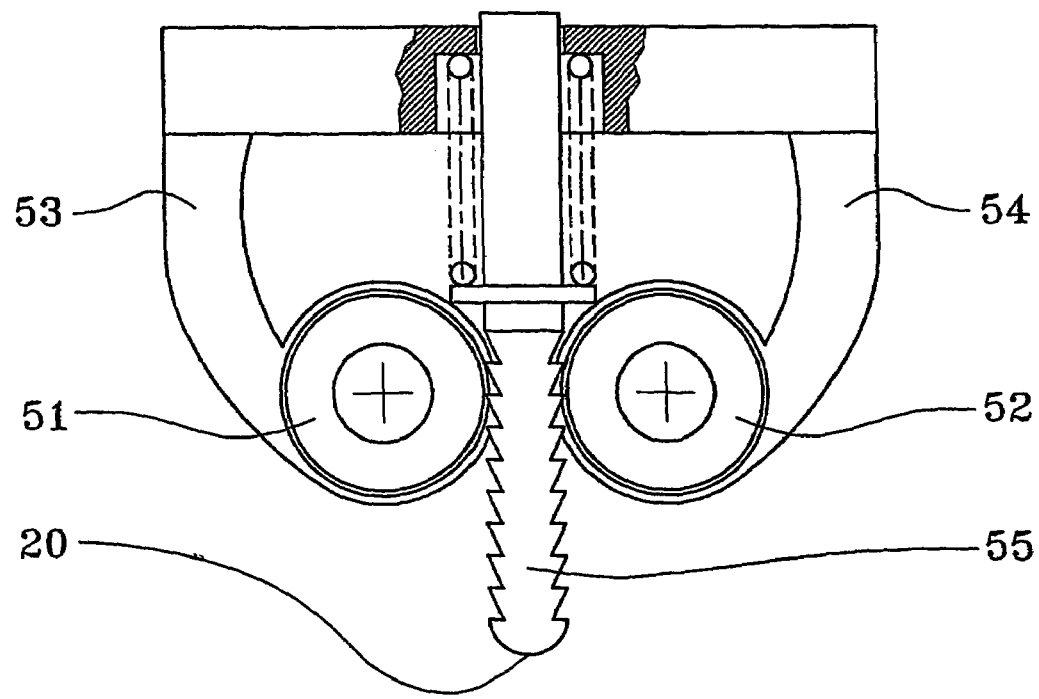
FIG. 7 is a diagrammatic section view of said brake system.
Figure 8:
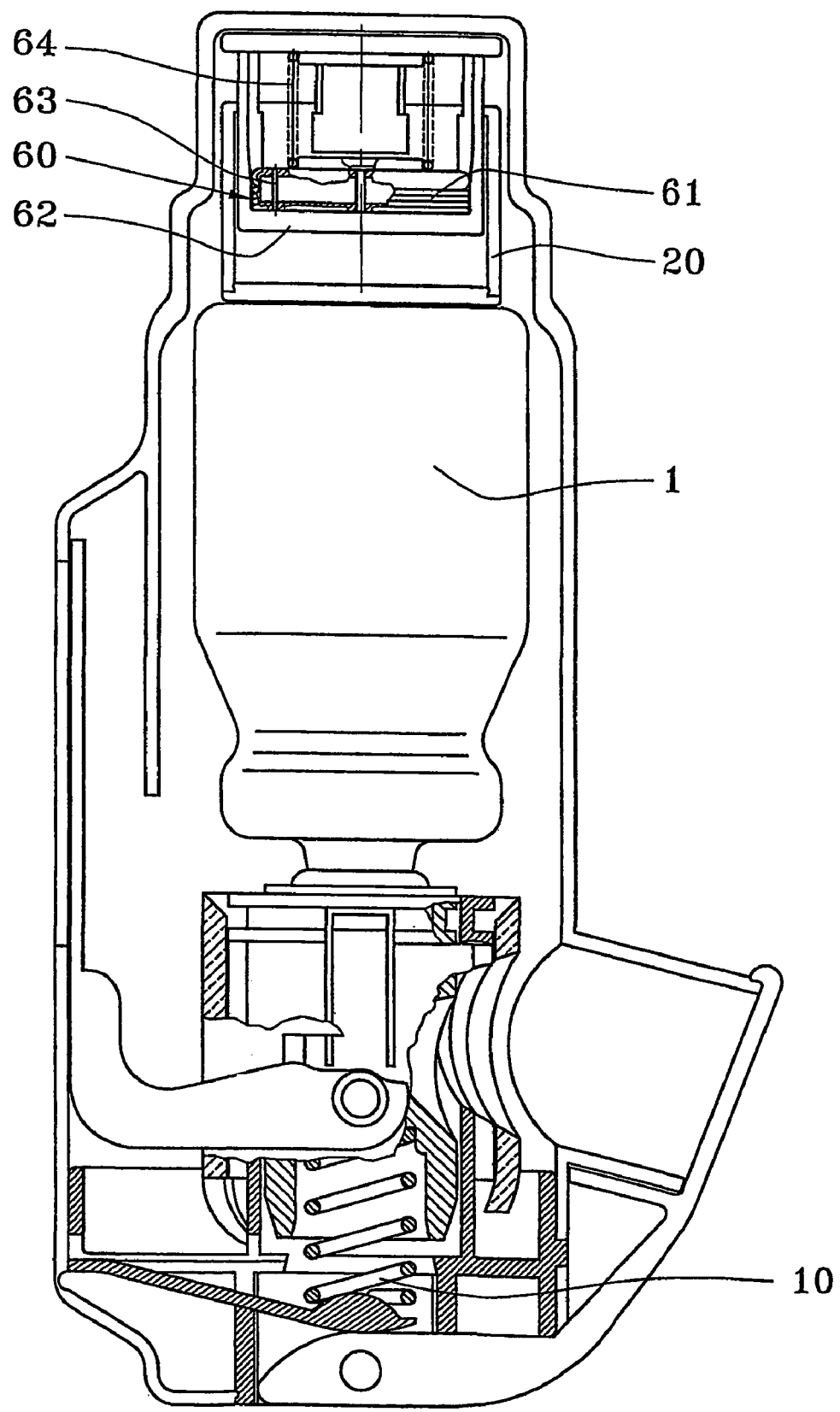
FIG. 8 is a variant embodiment of said second embodiment of the invention, before the valve is actuated.
Figure 9:
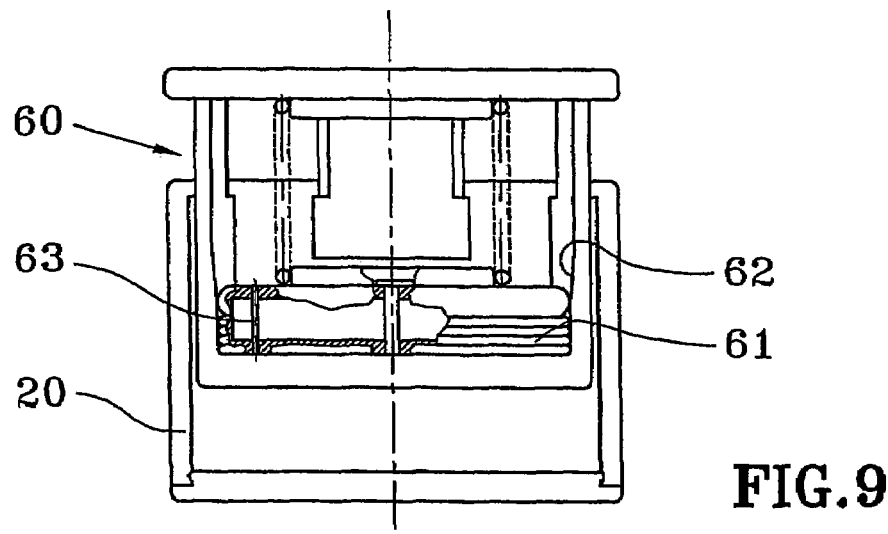
FIG. 9 is a diagrammatic section view of a detail of the pneumatic brake system of FIG. 8, before the device is actuated.
Figure 10:
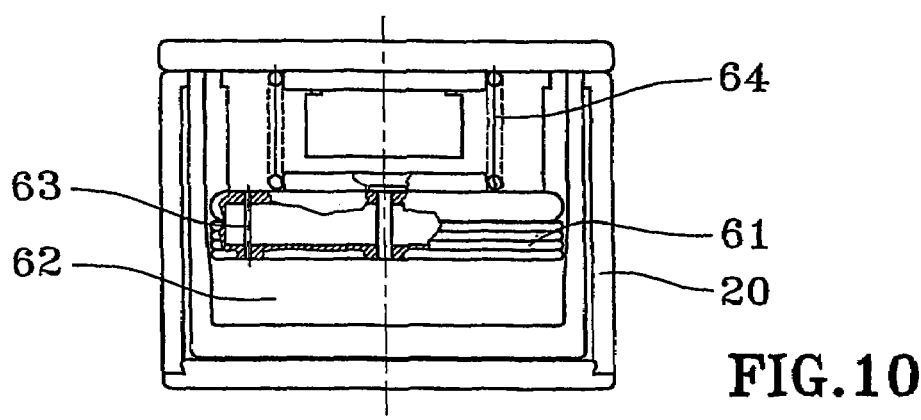
FIG. 10 is a view similar to the FIG. 9 view, while the device is being actuated.
Figure 11:
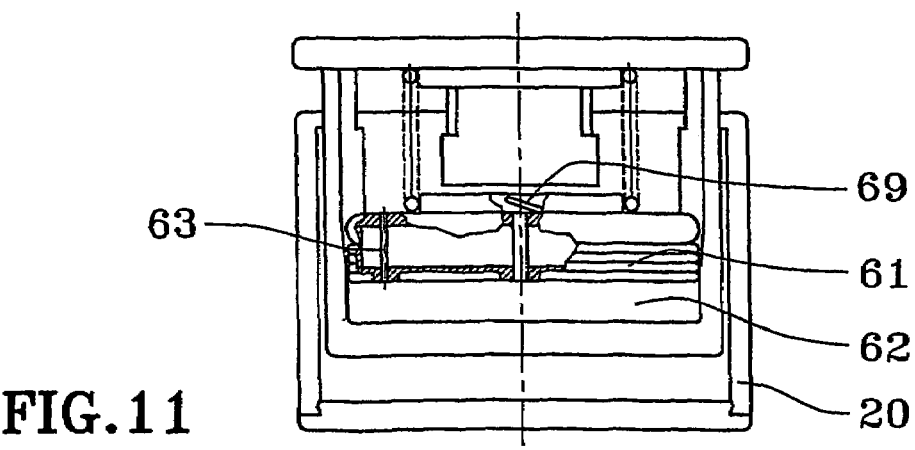
FIG. 11 is a view similar to FIGS. 9 and 10, after the device has been actuated.

A second embodiment of the invention is described below with reference to FIGS. 5, 6, and 7. In this second embodiment, a valve member release system is provided that has a brake device acting on that one of the elements comprising the valve member and the reservoir which is not subjected to the resilient force from the resilient element 10 of the breath-actuated trigger system, i.e. on that element which remains stationary during actuation. The brake device makes it possible for that portion of the BAI which is normally held stationary during actuation of the valve to move slowly and in predetermined manner. The acceleration delivered by the brake device is significantly less than the acceleration of the movement of the valve member relative to the reservoir while the metering valve is being actuated, under drive from the resilient element of the breath-actuated trigger system, so that the valve member is brought very rapidly into its dispensing position for dispensing the fluid contained in the metering chamber of the valve, while the above-mentioned predetermined slow movement makes it possible to release the valve member within a predetermined time which is dependent on the effectiveness of the brake device, and independent of the position of the resilient element of the breath-actuated trigger system.

Figure 5:
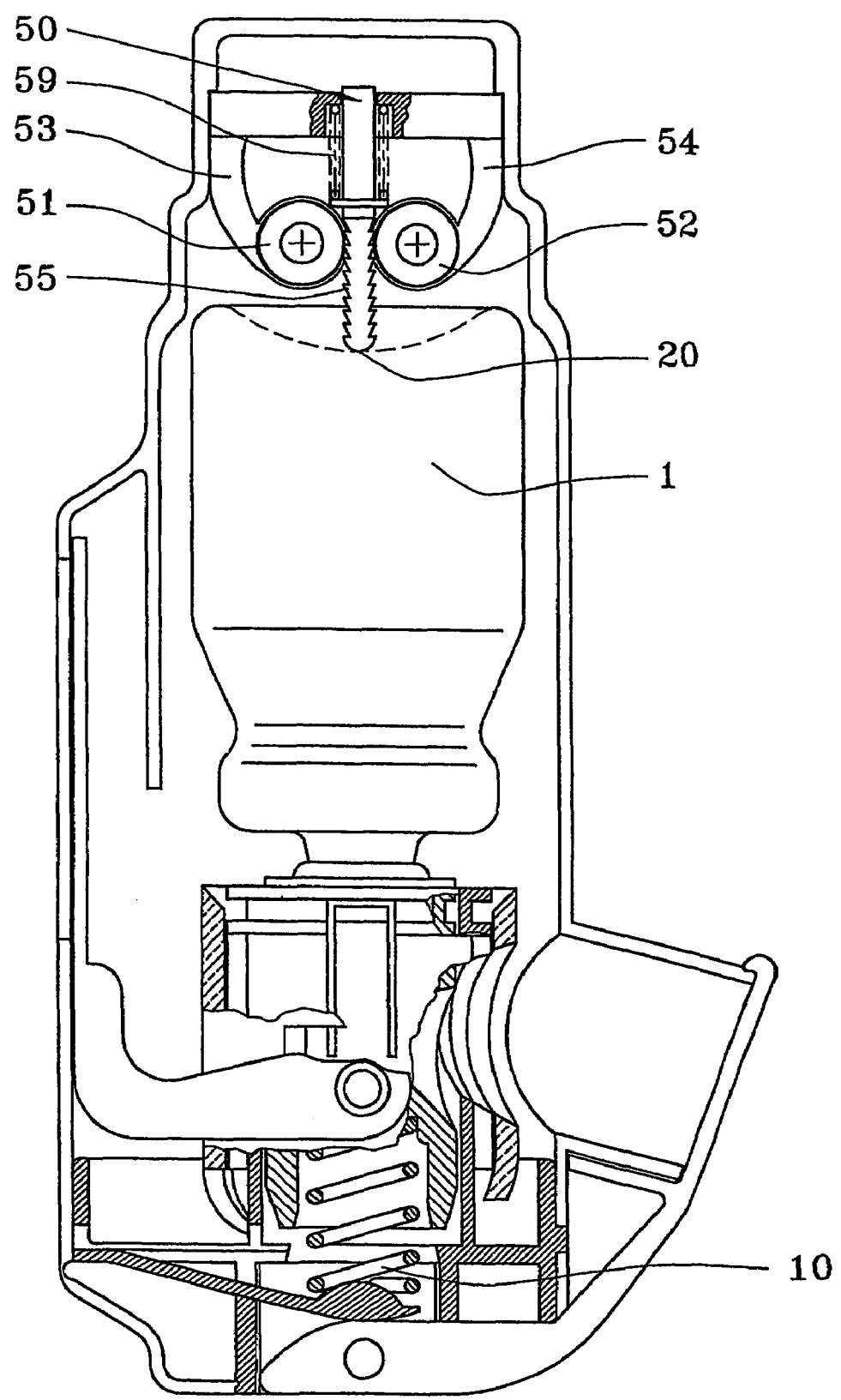
FIG. 5 is a diagrammatic section view of a second embodiment of the fluid dispenser device of the present invention, before the valve is actuated.

FIG. 5 shows an embodiment of a brake device 50 of the mechanical type. The brake 50, which, in this example, co-operates with the end-wall of the reservoir 1, has a moving element such as a rod 55 whose end in contact with the end-wall of the reservoir 1 forms the locking element 20. The rod 55 is preferably serrated and can slide between two friction wheels 51 and 52 which are preferably made of an elastomer material. Advantageously, as shown more particularly in FIG. 7, each friction wheel 51, 52 is secured to a respective semi-rigid arm 53 and 54 which can flex inwards, thereby causing the two wheels 51 and 52 to move closer together. Thus, before the user actuates the fluid dispenser device, by triggering the trigger system by inhaling, the assembly formed by the reservoir and by the metering valve 2 is pushed against the brake 50 by the resilient element 10 of the trigger system, said end-wall of the reservoir being retained by the locking element 20 formed by the end of the rod 55. Said rod is thus pushed between the two wheels 51 and 52. The presence of the serrations on the rod 55 acts to stimulate flexing of the flexible arms 53 and 54 and thus to bring the two wheels 51 and 52 towards each other to increase the friction force exerted on the rod 55, thereby achieving the desired braking. The movement of the reservoir 1 while the resilient element 10 of the trigger system is exerting thrust is thus braked by the brake 50, so that the valve member 3 of the valve 2 firstly reaches its dispensing position very rapidly so as to dispense the fluid, while the reservoir 1 moves much more slowly at the end of the movement of the rod 55 between the two wheels 51 and 52. Thus, when the locking element 20 is in the unlocking position, the valve member 3 is returned to its rest and filling position under drive from the return spring (not shown) of the metering valve. By means of the brake 50, the valve member 3 automatically returning to its rest position does not take place immediately after the fluid has been dispensed, but rather after a certain delay corresponding to the action of the brake 50 on the end-wall of the reservoir 1.

Advantageously, a return spring 59 is also provided for returning the brake 50 to its starting position when the resilient element 10 of the breath-actuated trigger system is returned to its rest position, in particular by closing the lid of the mouthpiece. The shape of the serrations on the serrated rod 55 is preferably organized so that, when it moves towards its unlocking position, it causes the elastomer wheels 51 and 52 to move towards each other under the effect of the flexible arms 53 and 54 flexing, so as to increase the friction force. Conversely, when the rod returns to its locking position under drive from the return spring 59, said serrated rod slides easily between said two wheels 51 and 52, the serrations even tending to move them apart to facilitate this return to the starting position.

Another variant embodiment of the above-described brake is described below with reference to FIGS. 8 to 11, in which the brake is a pneumatic brake 60 rather than a mechanical brake. This brake 60 has a piston 61 connected to a locking element 20 which co-operates with the end-wall of the reservoir 1. Said piston 61, which is preferably provided with an elastomer covering, is mounted to slide in leaktight manner in a chamber 62, said chamber 62 or said piston 61 being provided with a small hole 63 of small diameter. In the example shown in FIGS. 8 to 11, the brake 60 operates by suction, i.e., in the rest position shown in FIGS. 8 and 9, the piston 61 is disposed against the end wall forming the chamber 62. When the user actuates the device and the reservoir 1 transmits the pressure exerted by the resilient element 10 of the trigger system to the locking element 20, said locking element causes the piston to move away from the end-wall of the chamber 62, thereby generating suction between said end wall and said piston 61, the orifice 63 of small diameter enabling air to penetrate into said chamber 62 at a slow speed only, so that said piston 61 and thus the locking element 20 can move only slowly, thereby providing the required braking. Naturally, the effectiveness of the brake depends on the dimensions of the orifice 63 and of the chamber 62.

Advantageously, the pneumatic brake is also provided with a return spring 64 and with a non-return valve 69 which makes it possible for the piston to be returned rapidly to its starting position when the resilient element of the trigger system is returned manually by the user to its rest position (in particular by closing the lid).

Although the example of the pneumatic brake is described with reference to a system operating by suction, it is clear that the pneumatic brake of FIGS. 8 to 11 may be implemented so as to operate by compression. In which case, the piston 61 is in the rest position away from the end-wall of the chamber 62, and, when the device is actuated, it is urged resiliently towards said end-wall so that the air contained inside the chamber 62 can escape only through said orifice of small diameter 63, which can take place only slowly, thus providing the required braking.

In addition, it is also possible to imagine implementing the brake system hydraulically, by replacing the air with any desired liquid, and by correspondingly adapting the dimensions of the chamber 62 and of the small-diameter orifice 63.

In a variant, it is also possible to use a gear system enabling the desired braking function to be provided.

The concept of the brake, an example of which is described above, is suitable provided that the resistance of the return spring (not shown) of the metering valve is not too high, and therefore that the load on the resilient element 10 of the breath-actuated trigger system, which load ultimately acts against the brake 50, is not too high. The higher the force applied to the brake, the lower the effectiveness of said brake.

Figure 12:
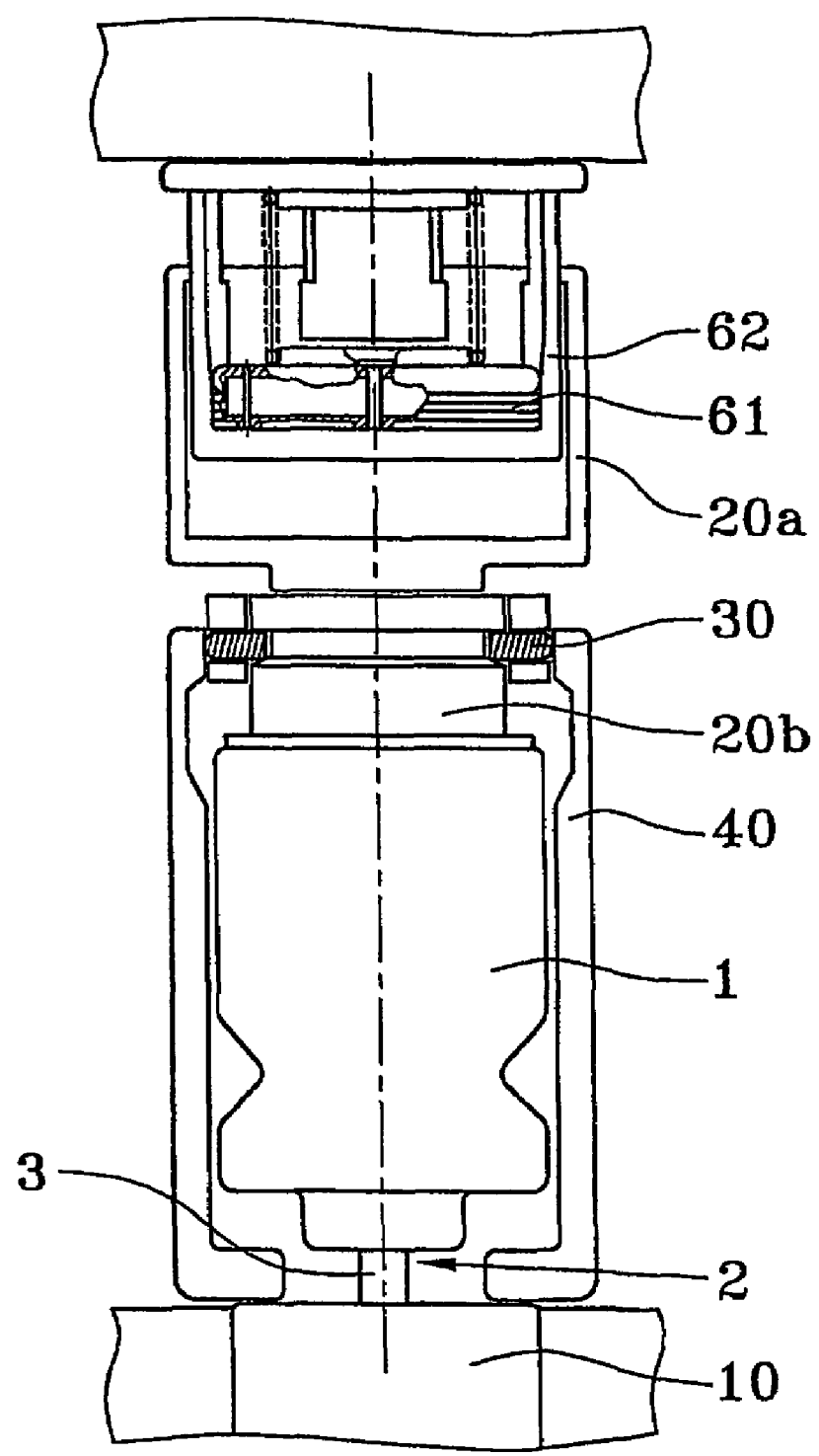
FIG. 12 is a diagrammatic section view of a third embodiment of the present invention, which combines the first and second embodiments.

A third embodiment of the present invention is described below with reference to FIG. 12, in which the system described above in the second embodiment, namely the brake, is combined with the system described in the first embodiment, namely a valve member release system acting as from the time at which valve member 3 of the valve reaches its dispensing position. This combination makes it possible to prevent the brake from operating as from the start of the actuation stroke of the valve member of the metering valve, said brake being actuated by said valve member release system only when the valve member reaches its dispensing position. Thus, while the valve member is traveling over its actuating stroke between its rest position and its actuating position, the brake is not yet active, and the reservoir remains stationary.

A first variant embodiment of such a combination is described below with reference to FIG. 12. Thus, it is a first locking element 20a that co-operates with the end-wall of the reservoir 1 and which is released from its locking position and moved towards its unlocking position only when the retaining element 30 is released from its retaining position. This takes place when the control element 40 reaches the releasing position, which corresponds to the valve member 3 being in the dispensing position. Thus, when the valve member 3 reaches its dispensing position and dispenses the fluid contained in the metering chamber, the first locking element 20a is released and can be moved axially upwards (as shown in FIG. 12) under drive from the return spring of the metering valve 2, but this movement is braked because the first locking element 20a co-operates with the second locking element 20b, which forms a part of the above-described pneumatic brake 60 by being connected to the piston 61 which is mounted to slide in the chamber 62. The valve member 3 returning to its rest position thus takes place slowly, which makes it possible to guarantee that all of the fluid contained in the metering chamber is dispensed. This makes it possible not necessarily to use a metering valve that is extremely fast, as it is when the valve member release system at the end of the actuating stroke of the valve member is used on its own.

Figures 13, 14:
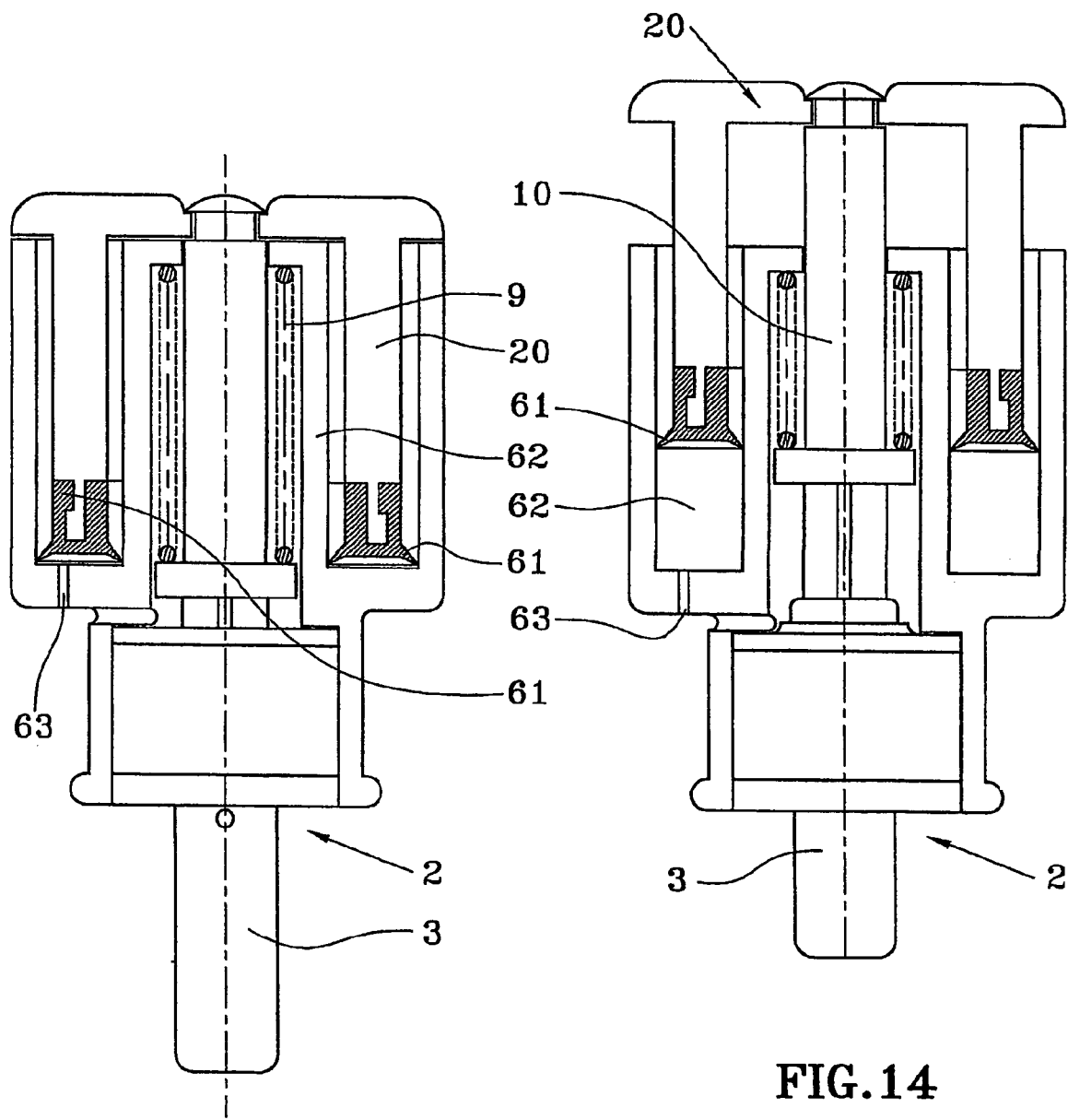
FIG. 13 is a diagrammatic section view of a variant embodiment of the pneumatic brake system, before the device is actuated.
FIG. 14 is a view similar to FIG. 13, after the device is actuated.

FIGS. 13 and 14 show a hydraulic brake system which is applied directly to the metering valve 2 and which can be used in a combination such as the combination described with reference to FIG. 12, with a valve member release system acting when the valve member reaches its dispensing position. In this embodiment shown in FIGS. 13 and 14, the valve 2 is of the standard type, and the valve body is modified to form an annular chamber 62 which receives an annular piston 61 provided with a sealing lip and which can slide in leaktight manner in said chamber 62. The chamber 62 is provided with a small hole 63 of small diameter, and the piston 61 is connected to the valve member stem, that is designated by numerical reference 10 in these figures, since the resilient element 10 of the breath-actuated trigger system, which acts on the valve member at the time of dispensing, by transmitting its force directly to the valve member 3 and thus to the valve member stem 10 connected to the piston 61, is not shown in FIGS. 13 to 14. The valve member stem 10 is also connected to the locking element 20 which forms the coupling between the valve member stem 10 and the piston 61. The valve member stem 10 is also connected directly to the return spring 9 of the metering valve 2, in conventional manner.

Thus, while the metering valve 2 is being actuated, the piston 61 slides upwards (as shown in FIGS. 13 and 14) in the chamber 62 without any difficulty, the sealing lip of the piston acting as a non-return valve which enables the fluid contained in the metering valve to penetrate without any difficulty into the chamber 62. When the valve member 3 is returned to its rest position, which is made possible once it has reached its dispensing position, by means of the first valve member release system which acts from this position, as described above, the piston 61 is thus forced to return to its rest position (shown in FIG. 13) by the return spring 9 of the metering valve, but it must overcome the resistance of the liquid which must escape from the chamber 62 through the small-diameter orifice 63, because, during its return stroke, the piston 61 slides in leaktight manner in said chamber 62. The braking effect required is thus provided very simply in this example directly in the metering valve. It should be noted that this valve may be implemented independently of the breath-actuated trigger system.

FIGS. 15 to 17 show a fourth embodiment of the present invention, in which provision is made to use a "delay system", said delay system delaying actuation of the valve member release system described with reference to FIGS. 1 and 2 by a predetermined time. This means that the valve member release system does not act as soon as the valve member 3 reaches its dispensing position, but a brake system 50 or 60 such as those described with reference to FIGS. 5 to 11, co-operates with the control element 40, so that said control element takes a certain predetermined time to release the retaining member 30, and thus the first locking element 20a. For this purpose, the control element 40, which makes it possible to trigger the valve member release system, by enabling the retaining member 30 to move from its retaining position towards its non-retaining position, so as to release the first locking element 20a, is made up of a first control element portion 48 and of a second control element portion 49, the two portions being interconnected by a spring 45 which is preferably of low stiffness. The first portion 48 of the control element co-operates with the resilient element 10 and the second portion 49 of the control element co-operates firstly with the retaining member 30 and secondly with a second locking element 20b secured to the brake system 60. Thus, when the device is actuated, the resilient element 10 of the breath-actuated trigger system moves the valve member 3 from its rest position to its dispensing position, and, at the same time, moves the first portion 48 of the control element, thereby compressing the spring 45. Since the spring 45 is much less powerful than the spring of the resilient element 10, the movement of the valve member 3 towards its dispensing position is not slowed down or braked at all by the presence of the spring 45. When the valve member 3 reaches its dispensing position, the spring 45 then acts on the second portion 49 of the control element, which moves the second locking element 20b, this movement being braked by the brake system 60. It is thus only after a certain delay, which is predetermined by the characteristics of the spring 45 of the brake 60, that the second portion 49 of the control element 40 reaches the position in which the retaining member 30 is released, enabling the first locking element 20a to move towards its unlocking position.

The embodiment shown in FIGS. 15 to 17 uses a pneumatic brake system and a mechanical spring delay system, but it is quite possible to use a delay system of the electronic or electromechanical type. In which case, the brake could be replaced by an electronic delay system, and the valve member release system could be replaced by an electromagnet which causes an element to slide when it is actuated, which element is equivalent to the second portion 49 of the control element 40.

Although the present invention is described with reference to various embodiments of it that are given by way of non-limiting example, clearly the person skilled in the art may make modifications to it without going beyond the ambit of the present invention as defined by the accompanying claims.

The invention claimed is:

1. A fluid dispenser device comprising
a reservoir (1) containing fluid and a propellant gas,
a metering valve (2) mounted on said reservoir and comprising a metering chamber and a valve member (3) mounted to move between a dispensing position and a rest position, and
an automatic trigger system for actuating said valve, said trigger system comprising a resilient element (10) formed by or secured to a spring, said resilient element capable of being moved manually by the user into a cocked position in which it is held under tension, actuation of the trigger system releasing said resilient element (10) which then moves to an actuating position while exerting a force adapted to moving the valve member (3) of the valve (2) towards its dispensing position, said resilient element (10) then being returned manually by the user from its actuating position to its rest position in which it no longer urges said valve member towards its dispensing position,
said fluid dispenser device further comprises a mechanical valve member release system which co-operates with the reservoir (1) or with the valve member (3) of the valve (2) so that, after dispensing the fluid contained in the metering chamber of the valve, said valve member (3) is mechanically released from the force exerted by said resilient element (10) of the trigger system, so that, after the device is actuated, said valve member (3) is returned to its rest position by the return spring of the valve, independently of the position of said resilient element,
said valve member release system comprising a locking element (20) co-operating with one of the valve member (3) and the fluid reservoir (1), said locking element (20) being mounted to move between a locking position, in which the valve member (3) can be brought into its dispensing position by said resilient element (10) of the trigger system, and an unlocking position, in which the valve member (3) is brought into its rest position independently of the position of said resilient element (10), said locking element (20) being urged to its unlocking position after the trigger system has been actuated, the valve member release system including a retaining member (30) that can be moved from a retaining position in which it retains said locking element (20) in its locking position, and a non-retaining position in which it does not retain said locking element (20) in its locking position, said retaining member (30) being moved towards its non-retaining position when the valve member (3) reaches its dispensing position, said valve member release system including a control element (40) co-operating firstly with the valve member (3) and secondly with the retaining member (30) so that when the valve member (3) reaches its dispensing position, the control element (40) makes it possible to move the retaining member (30) to its non-retaining position so that the locking element (20) is moved into its unlocking position, and the valve member is returned to its rest position by the return spring of the valve, said control element being a sleeve surrounding said retaining member externally.

2. A device according to claim 1, in which said retaining member (30) is resiliently deformable and said control element includes a first inside diameter (41) co-operating with the retaining member (30) to prevent it from deforming and thus to hold it in its retaining position, and a second inside diameter (42) greater than said first inside diameter (41), which co-operates with said retaining member (30) when the valve member (3) reaches its dispensing position, then making it possible to deform said retaining member (30) towards its non-retaining position.

3. A device according to claim 1, in which said locking element (20) includes a brake device (50, 60) adapted to slow down the movement of said locking element (20) towards its unlocking position, after the trigger system has been actuated.

4. A device according to claim 3, in which said brake device (50) is mechanical and includes a moving element (55) connected to said locking element (20), and that slides with friction against or between one or more brake members (51, 52).

5. A device according to claim 4, in which said moving element is a preferably serrated rod (55), and said brake members comprise two preferably elastomer wheels (51, 52), said rod (55) sliding with friction between said wheels (51, 52).

6. A device according to claim 5, in which each wheel (51, 52) is secured to a respective deformable arm (53, 54) so that when the rod (55) slides between said wheels, each arm (53, 54) deforms so that said wheels (51, 52) come towards each other, thereby increasing the friction exerted on said rod (55) to perform the braking.

7. A device according to claim 3, in which said brake device (60) is pneumatic and/or hydraulic.

8. A device according to claim 7, in which said brake device (60) includes a piston (61) connected to said locking element (20), said piston (61) sliding in leaktight manner in a chamber (62), said chamber (62) or said piston (61) being provided with a small orifice (63) so that gas or liquid can flow only slowly into or out from said chamber (62), thereby causing said piston (61) to move slowly.

9. A device according to claim 1, in which the locking element comprises a first locking element (20a) moved to its unlocking position when the valve member (3) reaches its dispensing position, and a second locking element (20b) provided with a brake system (50, 60), and urged into its unlocking position by said first locking element (20a) when it is in the unlocking position, so that the brake system (50, 60) is actuated only once the valve member (3) is in its dispensing position.

10. A device according to claim 9, in which said first locking element (20a) co-operates firstly with the end-wall of the reservoir (1) and secondly with said second locking element (20b) which is secured to said brake (50, 60).

11. A device according to claim 1, in which said valve member release system includes a delay system adapted to release the valve member (3) of the metering valve (2) after a predetermined delay time after the valve member (3) has reached its dispensing position.

12. A device according to claim 11, in which the locking element comprises a first locking element (20a) retained by a retaining member (30) itself co-operating with a control element (40), said control element (40) having a first portion (48) secured to the resilient element (10) of the trigger system, and a second portion (49) co-operating firstly with said retaining member (30), and secondly with a second locking element (20b) provided with a brake system (50, 60), a resilient member (45) of low stiffness, such as a spring, being interposed between said first and second portions (48, 49) of the control element (40), so that said first locking element (20a) can move towards its unlocking position only after a delay time predetermined to enable said valve member (3) of the valve (2) to return to its rest position, said delay time corresponding to the time necessary for the second locking element (20b) to move into its unlocking position, against said brake system (50, 60) under drive from said resilient member (45), thereby moving said second portion (49) of the control element (40) into the position in which the retaining member (30) can deform into its non-retaining position, so as to enable the first locking element (20a) to move into its unlocking position.

13. A device according to claim 11, in which said delay system is electronic or electromechanical.

14. The device of claim 1, wherein the automatic trigger system is actuated by the user inhaling.

15. A fluid dispenser device comprising:
a reservoir containing a fluid;
a metering valve mounted on the reservoir;
a valve member moveable between a dispensing position and a rest position;
a resilient member;
wherein when the resilient member is cocked, actuation of a trigger releases the resilient member so that it exerts a force on the valve member to move the valve member from the dispensing position to the rest position; and
wherein a release system mechanically releases the valve member from the force exerted by the resilient member by returning the valve member to its rest position independently of the position of the resilient member, and
wherein the fluid dispenser device further comprises:
a locking element attached to the reservoir;
a retaining member; and
a control member surrounding externally the reservoir and the locking element;
wherein the control member comprises a first diameter portion and a second diameter portion, the first diameter being larger than the second diameter and wherein the locking element comprises a third diameter portion and a fourth diameter portion, the third diameter being larger than the fourth diameter;
wherein before the trigger is actuated, the retaining member is engaged with the fourth diameter portion of the locking element and contacts the control member at the second diameter portion; and
wherein after the trigger is actuated, the retaining member contacts the third diameter portion of the locking element and the first diameter portion of the control member.

16. The fluid dispenser device of claim 15, wherein the resilient member is manually cocked.

17. The device of claim 15, wherein said control member is a sleeve.

* * * * *